United States Patent
Schreiber et al.

(10) Patent No.: US 9,360,438 B2
(45) Date of Patent: Jun. 7, 2016

(54) METHOD FOR RADIOGRAPHICALLY INSPECTING A COMPONENT BY MEANS OF X-RAY BEAMS USING A SMOOTHING AGENT AND SMOOTHING AGENT FOR CARRYING OUT THE METHOD

(75) Inventors: Karl Schreiber, Am Mellensee (DE); Josef Geitner, Stahnsdorf (DE)

(73) Assignee: Rolls-Royce Deutschland Ltd & Co KG (DE)

(*) Notice: Subject to any disclaimer, the term of this patent is extended or adjusted under 35 U.S.C. 154(b) by 555 days.

(21) Appl. No.: 13/814,582

(22) PCT Filed: Aug. 9, 2011

(86) PCT No.: PCT/EP2011/003984
§ 371 (c)(1),
(2), (4) Date: Apr. 1, 2013

(87) PCT Pub. No.: WO2012/019754
PCT Pub. Date: Feb. 16, 2012

(65) Prior Publication Data
US 2013/0202088 A1    Aug. 8, 2013

(30) Foreign Application Priority Data
Aug. 9, 2010 (DE) .......................... 10 2010 033 762

(51) Int. Cl.
*C09D 5/03* (2006.01)
*C09D 5/34* (2006.01)
*C09D 191/00* (2006.01)
(Continued)

(52) U.S. Cl.
CPC ................ *G01N 23/04* (2013.01); *C09D 5/032* (2013.01); *C09D 5/34* (2013.01); *C09D 191/00* (2013.01)

(58) Field of Classification Search
None
See application file for complete search history.

(56) References Cited

U.S. PATENT DOCUMENTS

| 753,310 A |   | 3/1904  | Price |
|-----------|---|---------|-------|
| 2,162,420 A |   | 6/1939  | Buckley |
| 2,916,623 A | * | 12/1959 | Ritchey .......................... 378/58 |

(Continued)

FOREIGN PATENT DOCUMENTS

| DE | 3609158  | 6/1987 |
|----|----------|--------|
| DE | 10201946 | 8/2003 |

(Continued)

OTHER PUBLICATIONS

Notification of Transmittal of Copies of Translation of the International Preliminary Report on Patentability dated Feb. 21, 2013 for counterpart PCT Application.

(Continued)

*Primary Examiner* — Joseph D Anthony
(74) *Attorney, Agent, or Firm* — Timothy J. Klima; Shuttleworth & Ingersoll, PLC

(57) ABSTRACT

The present invention relates to a method for radiographically inspecting a component by means of X-rays, where at least one component surface to be radiographed is provided with a surface structure, with at least the surface provided with the surface structure being smoothed by means of a smoothing material to level out the surface structure, with at least one organic compound and at least one metal powder being used as smoothing material, with the X-ray absorption behavior of the smoothing material essentially equaling the X-ray absorption behavior of the material of the component, as well as to a smoothing material for carrying out the method in accordance with Claim.

9 Claims, 1 Drawing Sheet

Figure 1:
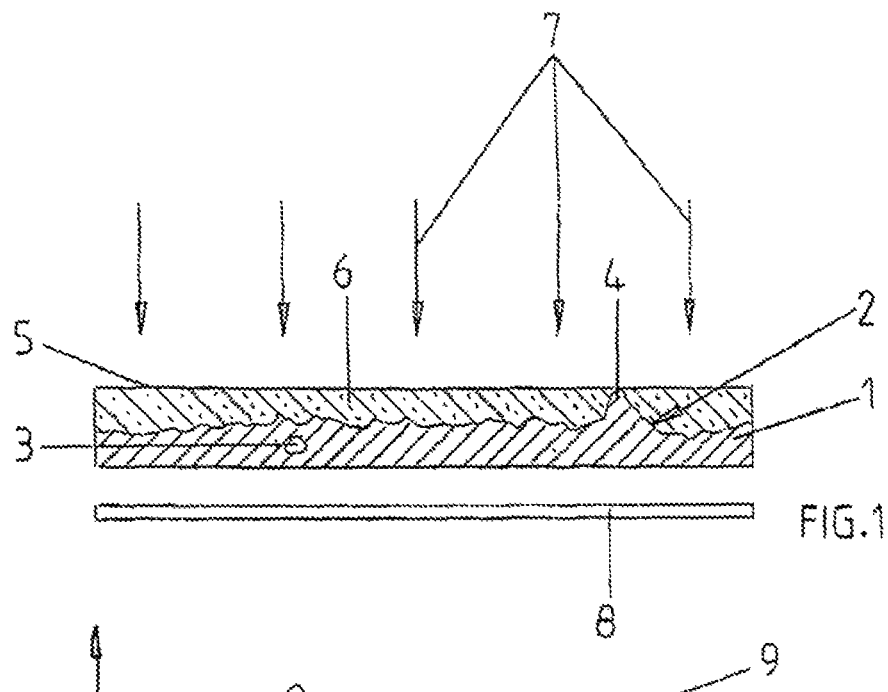

(51) Int. Cl.
  *C08K 3/08* (2006.01)
  *G01N 23/04* (2006.01)

(56) References Cited

U.S. PATENT DOCUMENTS

| | | | |
|---|---|---|---|
| 3,102,024 A | | 8/1963 | Knapp |
| 5,342,573 A | * | 8/1994 | Amano ................ B22F 1/0059 419/23 |
| 6,837,924 B2 | | 1/2005 | Breindl et al. |
| 8,012,373 B2 | * | 9/2011 | Walsh ................ C10M 125/04 106/14.05 |
| 2009/0159846 A1 | * | 6/2009 | Sugimoto ............ A23L 3/3436 252/188.28 |
| 2009/0270998 A1 | * | 10/2009 | Kokubo ................ A61F 2/28 623/23.55 |
| 2010/0255233 A1 | * | 10/2010 | Wakana ................ C08L 9/00 428/35.7 |
| 2010/0288978 A1 | * | 11/2010 | Walsh ................ C10M 125/04 252/389.52 |
| 2012/0033787 A1 | * | 2/2012 | Schreiber ............. G01N 23/04 378/58 |

FOREIGN PATENT DOCUMENTS

| | | | |
|---|---|---|---|
| DE | 10 2006 004 622 | | 8/2007 |
| DE | 102006005247 | | 8/2007 |
| EP | 0154271 | | 9/1985 |
| EP | 0346809 | | 12/1989 |
| EP | 0885269 | | 12/1998 |
| GB | 760617 | | 11/1956 |
| JP | 57204441 | | 12/1982 |
| WO | 9732939 | | 9/1997 |
| WO | WO/2009/057500 | * | 5/2009 ................ C08L 9/00 |

OTHER PUBLICATIONS

PCT International Search Report dated Dec. 6, 2011 from counterpart application.

German Search Report dated Aug. 9, 2010 from counterpart application.

* cited by examiner

METHOD FOR RADIOGRAPHICALLY INSPECTING A COMPONENT BY MEANS OF X-RAY BEAMS USING A SMOOTHING AGENT AND SMOOTHING AGENT FOR CARRYING OUT THE METHOD

This application is the National Phase of International Application PCT/IB2011/003984 filed Aug. 9, 2011 which designated the U.S.

This application claims priority to German Patent Application No. 102010033762.5 filed Aug. 9, 2010 and PCT Application No. PCT/IB2011/003984 filed Aug. 9, 2011, which applications are incorporated by reference herein.

This invention relates to a method for radiographically inspecting a component by means of X-rays, especially for automatic or automatable radiographic inspection, where in particular a component is tested which is provided on at least one surface to be radiographed with a surface structure, for example with a surface roughness created by a machining process.

The invention thus relates to a smoothing material for surface smoothing of components subjected to radiographic inspection using X-rays, in particular components made of low-alloy or high-alloy steels or titanium, aluminum or nickel-base materials, based on the fact that absorption and intensity of the radiation impinging on an X-ray film after having passed the component differ due to material defects.

A radiographic inspection, in particular by means of X-rays or gamma rays, is an imaging method for non-destructive material testing in which a component to be tested is subjected to radiation by X-rays and a projected image of the component is presented on an X-ray film or an X-ray detector. Due to the differing radiation absorption and to the correspondingly differing radiation attenuation, voids, inclusions, segregations, gas bubbles, cracks or bonding defects present in the component can be made discernible, for example in the form of a higher density of the X-ray film caused by the greater radiation intensity.

The detectability of material defects is impaired by edge blurring, i.e. by a penumbral area present around an imperfection, and by a low contrast (difference in density) which may be caused by scattered radiation from the electromagnetic waves impinging on an irregular and non-smooth component surface. However, an irregular surface geometry of the component to be inspected primarily leads to reduced radiation absorption in certain surface areas and correspondingly to high radiation intensity. The densities thus generated on the X-ray film do, however, not represent any relevant material defects, but rather falsify the inspection result and do not permit any exact recognition of material defects or any reliable automatic evaluation.

In the radiographic inspection, wave or particle beams are absorbed in an absorbing, homogeneous material. The probability of absorption per distance unit is identical at low energies in every penetration depth, with Lambert's Law applying. Absorption depends here on the properties of the absorbent material and on the energy of the radiation. From this, the absorption coefficient can be determined, from which in turn the thickness of the half-value layer can be calculated. During radiography of a component by means of X-rays or gamma rays, the probability for absorption is thus proportional to the thickness of the radiographed component. Consequently, surface structures, for example surface roughnesses, lead to an attenuation of the ray and hence can simulate a defect which is non-existent in the component of the material and is caused only by the different component thickness.

The result of the interferences caused by the surface structure is therefore attenuations of the ray which are reflected in the half-value thickness, which is inversely proportional to the absorption coefficient.

The object underlying the present invention is to provide a method for radiographic inspection of a component, in particular by means of X-rays or gamma rays, which while being simply and cost-effectively applicable, provides a high degree of precision for the detection of defects.

It is a particular object of the present invention to provide solution to the above problems by the combinations of the features described herein. Further advantageous embodiments of the invention will become apparent from the present description.

Radiographic inspection of components using X-rays or gamma rays is carried out on the basis that absorption and intensity of the radiation imping for example on an X-ray film after having passed the component differ due to material defects in the component, and that the density of the X-ray film is influenced by the radiation intensity.

The core of the invention is thus that an uneven component surface structure (surface topography), also causing differing radiation intensities, is covered with a smoothing layer made of a smoothing material and having the same X-ray absorption behaviour as the base material of the component, where the half-value thicknesses or volume-specific radiation absorptions of the component material and of the smoothing layer made from the smoothing material on the component surface are identical or nearly identical.

The invention thus provides that in components with a rough surface, the variously thick surface areas are smoothed by means of a smoothing layer made from the smoothing material in accordance with the invention. Surface areas (surface structures) of this type can for example be provided in the form of welds. Exact investigation and material testing are thus possible particularly when testing welds for pipes, pipelines or the like. Due to the smoothing in accordance with the invention, the different surface structures generate only insubstantial signals or none at all, so that even the most minor structure defects can be clearly discerned and identified. In accordance with the invention, therefore, a "physical smoothing" of the component to be tested is performed.

The smoothing material in accordance with the invention of the smoothing layer is selected such that it has an absorption behaviour for the X-rays or gamma rays which is equal to the absorption behaviour of the base material.

In a preferred embodiment of the invention, the smoothing layer includes a material that consists by around 35 to 45 percent by volume of at least one plastically deformable organic compound and by around 55 to 65 percent by volume of at least one metal powder, where the metal powder is predominantly made up of the base material of the component and an additional metal powder consisting of lead or iron.

By applying the smoothing layer in accordance with the invention onto the component to be tested and provided with the surface structure, a reduction of the radiation absorption or an increase in the radiation intensity due to an uneven surface topography is prevented. The density generated on the X-ray film or X-ray detector is due to internal material defects only. This allows exact and preferably also automated radiographic inspection, which is of crucial importance in particular for safety-relevant components.

Due to the metal powder proportion not exceeding 65 percent by volume, the smoothing material is sufficiently plastically deformable, so that it can be applied as a smoothing layer to the component surface and removed again after the radiographic inspection. The metal powder consists substantially of the base material of the component to be tested.

However, to achieve in the entire smoothing layer, including filler material and metal powder, a radiation absorption which matches that of the base material, i.e. to achieve the same half-value thickness in both the component and the smoothing layer, the metal powder made from the base material of the component contains a proportion of a metal powder with higher absorption capacity than the base material of the component, preferably iron or lead powder.

The smoothing layer in accordance with the invention is for example used in components of low-alloy steels and high-alloy steels and of titanium-base materials, aluminum-base materials and nickel-base materials.

In the following, the composition of the smoothing material is explained by way of examples. In each case, an assessment is given of the X-ray half-value thicknesses for various compositions of the radiographed material of a component with an X-ray radiation energy of 100 KEV:

EXAMPLE 1

Components of iron/steel and steels with less than 30% of alloying constituents, for example forged, rolled or cast steel. A component of this type has a half-value thickness of 2.5 mm.

A preferred smoothing material with a half-value thickness of 2.5 mm includes a proportion by volume of 1.8% for lead, a proportion by volume of 58.2% for iron and a proportion by volume of 40% for organic compound.

EXAMPLE 2

Aluminum and aluminum alloys with less than 20% of alloying constituents have a half-value thickness of 16 mm.

To do so, a smoothing material with a proportion by volume of 40% for organic compound and a proportion by volume of 59.83% for aluminum and a proportion by volume of 0.175% for lead is used. This leads to a half-value thickness of 16 mm.

Alternatively, a smoothing material with a proportion by volume of 40% for organic compound could have a proportion by volume of 55.5% for aluminum and a proportion by volume of 4.5% for iron. This also leads to a half-value thickness of 16 mm.

EXAMPLE 3

Titanium and titanium alloys with less than 15% of alloying constituents have a half-value thickness of 5.6 mm.

A smoothing material suitable for this purpose has, with a proportion by volume of 40% for organic compound, a proportion by volume of 59.27% for titanium and a proportion by volume of 0.73% for lead. This leads to a half-value thickness of 5.6 mm.

Alternatively, a smoothing material with a proportion by volume of 40% for organic compound and a proportion by volume of 31.3% for titanium and a proportion by volume of 28.7% for iron can be used. This also leads to a half-value thickness of 5.6 mm.

EXAMPLE 4

IN 718 (Inconel 718) has a half-value thickness of 2.0 mm.

A smoothing material suitable for this purpose has, with a proportion by volume of 40% for organic compound, a proportion by volume of 57.6% for IN 718 and a proportion by volume of 2.4% for lead. This leads to a half-value thickness of 2.0 mm.

In the embodiments described above, the organic compound can for example be designed such that it has wax as the basis and includes water, oil, NaCl, starch and/or kaolin as filler materials. The required kneadability of the finished smoothing material provided with the metal powders and the adhesive capacity on the base surface are adjusted by admixing water and oil. This enables the smoothing material in accordance with the invention to be applied to a surface of the component to be tested which is clean and grease-free in the usual way. The smoothing material is self-adhesive and can be removed for re-use without leaving residues after the radiographic inspection. Hence no adhesive is necessary and no gap forms between the smoothing material and the component.

In accordance with the invention, the smoothing material can be applied by means of a spatula or a brush, and it is also possible to apply it using rollers or in an automated or partially automated manner by means of a suitable application device. As a result, the smoothing material in accordance with the invention can also be applied for smoothing of very great irregularities, for example in thicknesses between 0.1 mm and 10 mm.

The organic filling compound in accordance with the invention corresponds in a preferred manner to the requirements according to DIN EN 71-7.

Since in accordance with the invention the smoothing material is a mixture of organic compound and metal powder, a metal powder is used in accordance with the invention that has a greater half-value thickness than the base material of the component to be inspected, so that the same half-value thickness of the smoothing material is obtained in total as in the component to be tested.

In accordance with the invention, it is furthermore particularly favourable when the particle size of the metal powder is no more than 10 μm. Up to this size, the individual particles of the metal powder are not identifiable as such, so that the smoothing material for the radiographic inspection is homogeneous.

With a smoothing layer produced from the smoothing material in accordance with the invention applied to the component to be examined, material defects such as voids, inclusions, segregations, gas bubbles, cracks or bonding defects can be precisely detected both visually and in an automated process.

The present invention is described in the following in light of the accompanying drawing showing an exemplary embodiment. In the drawing, FIG. 1 shows a schematic sectional view of a component to be tested, with smoothing layer applied, FIG. 2 shows a schematic representation of a density curve without smoothing layer applied, and FIG. 3 shows a schematic representation of the density curve with virtual smoothing layer.

A forged component 1 made of Inconel 718 (IN 718) with a non-smooth and uneven surface geometry (surface structure 2) and intended for radiographic inspection using X-rays is provided with a smoothing layer 6 consisting of 40 percent by volume of organic compound, 57.6 percent by volume of IN 718 powder and 2.4 percent by volume of lead powder. The smoothing layer 6 thus formed has a half-value thickness of 2.0 mm, matching exactly the half-value thickness of the component material (see FIG. 1).

The half-value thickness is the thickness of the material needed to halve the radiation intensity during irradiation with X-rays.

Figure 2:
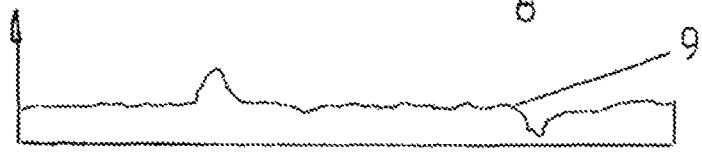
Figure 3:
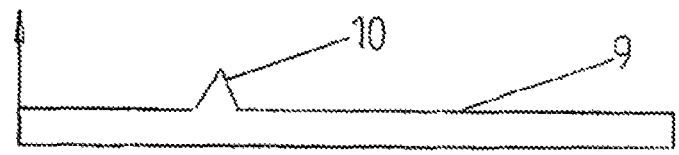

FIG. 2 shows a schematic representation of a density curve (X-ray image 9, density curve) that would result on an X-ray detector 8/X-ray film without the application of the smoothing layer in accordance with the invention. In particular it can be seen here that the X-rays 7 occurring do not clearly reproduce an internal defect 3 due to the uneven surface geometry (surface structure 2) of the component 1, since a schematically represented maximum elevation 4 also emits a clear signal.

In comparison to this, FIG. 3 shows a representation by analogy with FIG. 2 with the smoothing layer 6 in accordance with the invention (smoothed surface). The result of this is that the internal defect 3 generates a clearly discernible density peak 10, while the remaining surface structure 2 is not imaged because it is smoothed by the smoothing layer 6.

Due to the smooth nature of the component surface using the smoothing layer consisting of the indicated coating means, whose volume-specific radiation absorption matches that of the component material, internal defects present in the component were displayed on the X-ray film with sharp edges and visually easy to discern during the radiographic inspection, while densities of the X-ray film caused by uneven surfaces and leading to misinterpretations during the evaluation of the X-ray film were not detected. After the radiographic inspection, the smoothing layer was removed from the component surface.

It is understood that, as shown in FIG. 1, only one surface is provided with the smoothing material in accordance with the invention, if the other surface is sufficiently smooth and defect-free. It is however also possible to provide both surfaces (radiation entry surface and radiation exit surface) with the smoothing material in accordance with the invention.

LIST OF REFERENCE NUMERALS

1 Component
2 Uneven surface geometry/surface structure
3 Internal defect
4 Maximum elevation of 2
5 Smoothed surface
6 Smoothing layer/smoothing material
7 X-rays
8 X-ray detector
9 X-ray image, density curve
10 Density peak

What is claimed is:

1. An object for radiographic inspection, comprising:
a core component made of a base material of at least one chosen from iron, low-alloy steel, high-alloy steel, titanium, aluminum and a nickel-base material, the core component including an externally facing surface;
a smoothing layer applied to the externally facing surface of the core component, the smoothing layer made of a smoothing material comprising a mixture of 35 to 45 percent by volume of an organic compound and 55 to 65 percent by volume of a metal powder mixture, where the metal powder mixture is predominantly made up of the base material and an additional metal powder including lead or iron;
wherein a radiation absorption behavior of the smoothing material essentially equals a radiation absorption behavior of the base material;
wherein half-value thicknesses or volume-specific radiation absorptions of the base material and the smoothing material are identical or nearly identical.

2. The object for radiographic inspection of claim 1,
wherein the base material is steel with less than 30% of alloying constituents and a half-value thickness of 2.5 mm; and
wherein the smoothing material includes 40 percent by volume of organic compound, 58.2 percent by volume of iron powder and 1.8 percent by volume of lead powder, and has a half-value thickness of 2.5 mm.

3. The object for radiographic inspection of claim 1, wherein the smoothing material is plastically deformable.

4. The object for radiographic inspection of claim 3, wherein the smoothing material is kneadable.

5. The object for radiographic inspection of claim 1,
wherein the base material is aluminum or an aluminum alloy with less than 20% of alloying constituents and a half-value thickness of 16 mm; and
wherein the smoothing material includes 40 percent by volume of organic compound, 59.83 percent by volume of aluminum powder and 0.175 percent by volume of lead powder, and has a half-value thickness of 16 mm.

6. The object for radiographic inspection of claim 1,
wherein the base material is aluminum or an aluminum alloy with less than 20% of alloying constituents and a half-value thickness of 16 mm;
wherein the smoothing material includes 40 percent by volume of organic compound, 55.5 percent by volume of aluminum powder and 4.5 percent by volume of iron powder, and has a half-value thickness of 16 mm.

7. The object for radiographic inspection of claim 1,
wherein the base material is titanium or titanium alloy with less than 15% of alloying constituents and a half-value thickness of 5.6 mm; and
wherein the smoothing material includes 40 percent by volume of organic compound, 59.27 percent by volume of titanium powder and 0.73 percent by volume of lead powder, and has a half-value thickness of 5.6 mm.

8. The object for radiographic inspection of claim 1,
wherein the base material is titanium or titanium alloy with less than 15% of alloying constituents and a half-value thickness of 5.6 mm; and
wherein the smoothing material includes 40 percent by volume of organic compound, 31.3 percent by volume of titanium powder and 28.7 percent by volume of iron powder, and has a half-value thickness of 5.6 mm.

9. The object for radiographic inspection of claim 1,
wherein the base material is nickel-base material INCONEL 718 with a half-value thickness of 2.0 mm; and
wherein the smoothing material includes 40 percent by volume of organic compound, 57.6 percent by volume of INCONEL 718 powder and 2.4 percent by volume of lead powder, and has a half-value thickness of 2.0 mm.

* * * * *